(12) United States Patent
Roth et al.

(10) Patent No.: US 6,699,685 B1
(45) Date of Patent: Mar. 2, 2004

(54) **METHOD, TEST MEDIA AND CHROMOGENIC COMPOUNDS FOR IDENTIFYING AND DIFFERENTIATING GENERAL COLIFORMS AND *ESCHERICHIA COLI* BACTERIA**

(75) Inventors: Jonathan N. Roth, Goshen, IN (US); Wilfred J. Ferguson, Lakewood, OH (US)

(73) Assignee: RCR Scientific, Inc., Goshen, IN (US)

( * ) Notice: Subject to any disclaimer, the term of this patent is extended or adjusted under 35 U.S.C. 154(b) by 1,826 days.

(21) Appl. No.: 08/394,608

(22) Filed: Feb. 27, 1995

Related U.S. Application Data

(62) Division of application No. 08/024,212, filed on Mar. 1, 1993, now Pat. No. 5,393,662, which is a division of application No. 07/512,188, filed on Apr. 20, 1990, now Pat. No. 5,210,022.

(51) Int. Cl.$^7$ ................................................. C12Q 1/04
(52) U.S. Cl. ........................... 435/30; 435/18; 435/29; 435/34; 435/252.8
(58) Field of Search ........................... 435/38, 34, 29, 435/18, 252.8

(56) References Cited

U.S. PATENT DOCUMENTS

| | | | |
|---|---|---|---|
| 3,496,066 A | 2/1970 | Berger et al. ................. | 435/38 |
| 3,870,601 A | 3/1975 | Warren et al. ................. | 435/38 |
| 3,936,356 A | 2/1976 | Janin ............................ | 435/38 |
| 3,957,584 A | 5/1976 | Kronish et al. ............... | 435/88 |
| 4,275,149 A * | 6/1981 | Litman ......................... | 435/7 |
| 4,351,823 A | 9/1982 | Rubin .......................... | 424/9 |
| 4,503,143 A | 3/1985 | Gerber et al. ................. | 435/7 |
| 4,556,636 A | 12/1985 | Belly et al. ................... | 435/34 |
| 4,591,554 A | 5/1986 | Koumura et al. ............. | 435/18 |
| 4,603,108 A | 7/1986 | Bascomb ...................... | 435/34 |
| 4,673,638 A | 6/1987 | Grosch et al. ................ | 435/34 |
| 4,861,709 A | 8/1989 | Ulitzur et al. ................. | 435/6 |
| 4,925,789 A * | 5/1990 | Edberg ......................... | 435/38 |
| 5,393,662 A * | 2/1995 | Roth et al. .................... | 435/38 |

OTHER PUBLICATIONS

Watkins et al., *Appl. Environ. Microbiol.*, 54:1874–1875 (1988).

Ley et al., *Can. J. Microbiol.*, 34:690–693 (1987).

Sadler et al., *J. Am. Chem. Soc.*, 78:1251–1255 (1955).

Sales Brochure of Access Medical Systems, Inc., Cat. # IS–001 1/88 for Colilert MPN.

"Studies in Enzyme Cytochemistry III. Relationships Between Solubility, Molecular Association and Structure in Indigoid Dyes", Holt et al, Proc. Royal Soc. London, vol. 148B, pp. 495–505 (1958).

"Membrane Filter Method for Enumerating *Escherichia coli*", Dufour et al, Applied and Environmental Microbiology, vol. 41, No. 5, pp. 1152–1158 (May 1981).

"Membrane Filter Method for the Enumeration of Chlorine Damaged Coliforms in Drinking Water", Duncanson et al, Microbiology Dept., Univ. of Rhode Island.

* cited by examiner

Primary Examiner—Leon B. Lankford, Jr.
(74) Attorney, Agent, or Firm—Roylance, Abrams, Berdo & Goodman, L.L.P.

(57) ABSTRACT

A chromogenic β-galactosidase substrate producing an insoluble precipitate of a first color when reacted upon by β-galactosidase and a chromogenic β-glucuronidase substrate producing an insoluble precipitate of a second, contrasting color when reacted upon by β-glucuronidase are combined in a test medium for quantitatively identifying and differentiating general coliforms and *E. coli*. The β-galactosidase substrate 5-bromo-4-chloro-3-indolyl-β-D-galactopyranoside which produces an indigo blue precipitate when reacted upon by β-galactosidase may be used with one of the novel compounds 6-chloroindolyl-β-D-glucuronide, 4,6-dichloroindolyl-β-D-glucuronide, 6,7-dichloroindolyl-β-D-glucuronide, and 4,6,7-trichloroindolyl-β-D-glucuronide, which produce mauve or magenta precipitates when reacted upon by β-glucuronidase. The β-glucuronidase substrate 5-bromo-4-chloro-3-indolyl-β-D-glucuronide, which produces an indigo blue precipitate when reacted upon by β-glucuronidase may be used with one of the novel compounds 6-chloroindolyl-β-D-galactoside, 4,6-dichloroindolyl-β-D-galactoside, 6,7-dichloroindolyl-β-D-galactoside, and 4,6,7-trichloroindolyl-β-D-galactoside which produce mauve or magenta precipitates when reacted upon by β-galactosidase.

20 Claims, 1 Drawing Sheet

METHOD, TEST MEDIA AND CHROMOGENIC COMPOUNDS FOR IDENTIFYING AND DIFFERENTIATING GENERAL COLIFORMS AND ESCHERICHIA COLI BACTERIA

This application is a divisional application of Ser. No. 08/024,212 filed on Mar. 1, 1993, now U.S. Pat. No. 5,393,662 which is a division of Ser. No. 07/512,188 filed on Apr. 20, 1990, now U.S. Pat. No. 5,210,022.

BACKGROUND OF THE INVENTION

1. Field of the Invention

The present invention relates to a method, test medium, and novel chromogenic compounds for quantitatively identifying and differentiating general coliforms and *Escherichia coli*.

2. Description of the Related Art

Currently, in microbiology, the presence of indicator organisms is widely used to determine the quality of various products. For example, in the analysis of water, food and dairy products, the presence of members of the "coliform" group as well as the presence of the bacterial species *Escherichia coli* are considered very significant quality indicators. Therefore, test methods to effective identify and enumerate these bacterial types are needed, and there is a continuing search for better, more accurate and simpler test methods in this area.

Numerous methods for determining, identifying and enumerating coliforms and *E. coli* currently exist, with varying degrees of accuracy and facility. Some test methods only indicate the presence or absence (P/A) of the organisms while some methods attempt to quantify the organisms in the test materials. Following are some of the current methods.

Violet Red Bile Agar (VRBA): This medium incorporates bile salts to inhibit non-coliforms. It also contains lactose with the pH indicator neutral red. As coliforms (especially *E. coli*) grow in the medium, the lactose is fermented with acid production and the neutral red in the area of the bacterial colony becomes a brick red color. Therefore, any colonies growing as a red color in 24–48 hours are considered to be coliforms. This medium is not easy to interpret and for *E. coli* quantification needs to be followed up by confirming tests such as brilliant green lactose broth fermentation or streaking on Eosin Methylene Blue Agar (EMBA). In spite of these shortcomings, VRBA is an approved method for testing dairy products.

The Most Probable Number (MPN) method: This method utilizes various broth (liquid) media in tubes. Samples to be tested are added in varying amounts to the broth media and after incubation, the tubes are checked for growth and gas formation. Estimates of the numbers (populations) of bacteria are determined from pre-existing tables. The method is in general use, but the results are given in a general range and therefore are riot very precise.

The Membrane Filter (MF) method: This method utilizes micropore filters through which samples are passed so that the bacteria are retained on the surface of the filter. It is used most often when bacterial populations are very small and a large sample is needed to get adequate numbers. The filter is then placed on the surface of a chosen medium, incubated and the bacterial colonies are counted and evaluated. This method is widely used and gives good results in general if combined with proper reagents and media, but is expensive and time-consuming. The MF method can be used well in combination with the new method described herein.

The Presence/Absence (P/A) test: This test, which involves the reagents O-nitrophenyl-β-D-galactopyranoside (ONPG), a β-galactosidase substrate and 4-methyl-umbelliferyl-β-D-glucuronide (MUG), a β-glucuronidase substrate, results in the determination of the presence or absence of general coliforms and *E. coli*. The test relies on the fact that generally all coliforms produce β-galactosidase, but only *E. coli* strains produce β-glucuronidase. If any coliforms are present, the broth medium turns a yellow color due to the activity of galactosidase enzyme on the ONPG material causing the release of a diffusible yellow pigment. If *E. coli* is present, the broth medium will demonstrate a blue fluorescence when irradiated with ultraviolet rays due to the breakdown of the MUG reagent with the release of the fluorogenic dye caused by the production of the glucuronidase enzyme. These reactions are very specific and allow both general coliforms and *E. coli* to be identified in a single test in a single sample. But, since both reagents produce diffusible pigments, the test has the disadvantage of not being directly quantitative for either bacterial type.

The reagent 5-bromo-4-chloro-3-indolyl-β-D-galactopyranoside (X-gal) is a known test compound for identifying coliforms. When acted on by the β-galactosidase enzyme produced by coliforms, X-gal forms an insoluble indigo blue precipitate. X-gal can be incorporated into a nutrient medium such as an agar plate, and if a sample containing coliforms is present, the coliforms will grow as indigo blue colonies. X-gal has the advantage over the compound ONPG, described above, in that it forms an insoluble precipitate, rather than a diffusible compound, thereby allowing the quantitative determination of coliforms.

Recently, a similar compound, 5-bromo-4-chloro-3-indolyl-β-D-glucuronide (X-gluc) has been developed for the identification of *E. coli*. When acted on by the β-glucuronidase enzyme produced by *E. coli*, X-gluc forms an insoluble indigo blue precipitate. X-gluc has the advantages over the compound MUG, described above, in that it forms an insoluble precipitate, rather than a diffusible compound, thereby allowing the quantitative determination of *E. coli*. Further, it does not require the use of ultraviolet light. X-gluc and its use to identify *E. coli* are described in Watkins, et al, Appl. Environ. Microbiol. 54:1874–1875 (1988). A similar compound, indoxyl-β-D-glucuronide, which also produces sharp blue colonies of *E. coli*, was described in Ley, et al, Can. J. Microbiol. 34:690–693 (1987).

X-gal and X-gluc have the disadvantage that they each contain the exact same chromogen and therefore they cannot be used together to identify and distinguish between both *E. coli* and general coliforms in a single test with a single sample. Both X-gal and X-gluc cause the formation of identically hued indigo blue colonies. A person using both reagents together would be able to quantitatively identify the total number of coliforms, the same as if X-gal were used alone, but would not be able to tell which of the colonies were *E. coli* and which were other coliforms besides *E. coli*.

SUMMARY OF THE INVENTION

A method has now been found for quantitatively identifying and differentiating microorganisms having β-galactosidase but not β-glucuronidase activity and microorganisms having β-glucuronidase activity, comprising the steps of combining a chromogenic β-galactosidase substrate capable of forming an insoluble precipitate of a first color upon reacting with β-galactosidase, a chromogenic β-glucuronidase substrate capable of forming an insoluble precipitate of a second color contrasting with the first color upon reacting with β-glucuronidase, and a nutrient base medium to form a test medium, inoculating the test medium with a sample to be tested for the presence of microorganisms, incubating the test medium, examining the test medium for the presence of colonies of the first color, such colonies being colonies of microorganisms having β-galactosidase but not β-glucuronidase activity, and the presence of colonies of the second color, such colonies being colonies of microorganisms having β-glucuronidase activity, and enumerating the microorganisms having β-galactosidase but not β-glucurosidase activity and the microorganisms having β-glucuronidase activity.

The advantages of the new method include the following. First, it allows the chromogenic differentiation between general coliforms, which have β-galactosidase activity, and E. coli, which additionally have β-glucuronidase activity, in the same test plate with the same sample. It is also quantitative so that exact counts of the numbers of viable organisms of each type are determined. This is much more meaningful than just a presence/absence test as levels of contamination can be determined. The new method does not require any special apparatus or equipment such as a UV light source or special filter apparatus. The new method is based on enzymatic reactions rather than fermentation reactions which are more difficult to interpret and less precise. Because the new method does not require inhibitors, there is the additional capability of quantifying the general microbial population along with general coliforms and E. coli. This is an important added feature.

A further aspect of this invention is the novel compound 6-chloroindolyl-β-D-glucuronide, which forms an insoluble magenta precipitate when reacted upon by β-glucuronidase that contrasts in color with the indigo blue precipitate formed by 5-bromo-4-chloro-3-indolyl-β-D-galactopyranoside (X-gal) by the action of β-galactosidase. 6-Chloroindolyl-β-D-glucuronide may be used together with X-gal in the method of this invention. General coliforms grow in a medium containing 6-chloroindolyl-β-D-glucuronide and X-gal as colonies having an indigo blue color whereas E. coli grow as colonies having a purplish or magenta color. Composition and test media having 6-chloroindolyl-β-D-glucuronide and 5-bromo-4-chloro-3-indolyl-β-D-galactoside for quantitatively identifying and differentiating general coliforms and E. coli are yet another aspect of this invention.

A further aspect of this invention is the novel compound 6-chloroindolyl-β-D-galactoside, which forms an insoluble magenta precipitate when reacted upon by β-galactosidase that contrasts with the indigo blue precipitate formed by 5-bromo-4-chloro-3-indolyl-β-D-glucuronide (X-gluc) or indoxyl-β-D-glucuronide by the action of β-glucuronidase. 6-Chloroindolyl-β-D-galactoside may be used together with X-gluc or indoxyl-β-D-glucuronide in the method of this invention. General coliforms grow in a medium containing 6-chloroindolyl-β-D-galactoside and either X-gluc or indoxyl-β-D-glucuronide as colonies having a magenta color whereas E. coli grow as colonies having an indigo blue color. Compositions and test media having 6-chloroindolyl-β-D-galactoside and either 5-bromo-4-chloro-3-indolyl-β-D-glucuronide or indoxyl-β-D-glucuronide for quantitatively identifying and differentiating general coliforms and E. coli are yet another aspect of this invention.

DETAILED DESCRIPTION OF THE INVENTION

Figure 1:
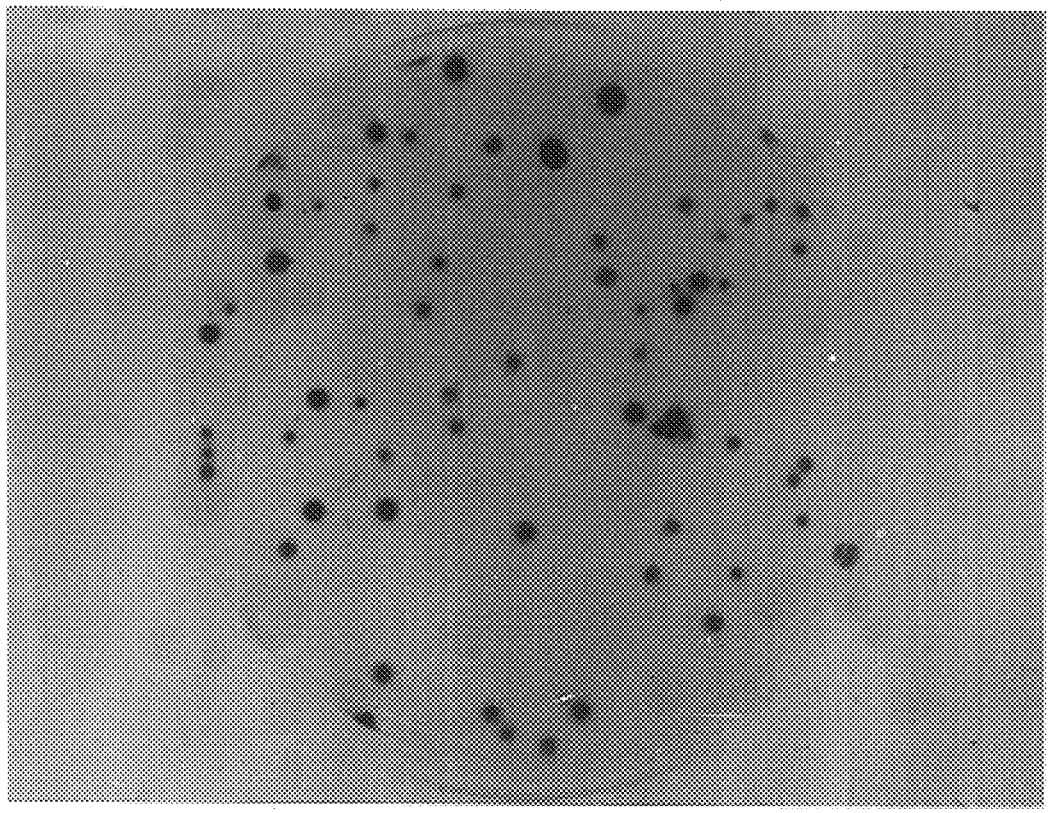
FIG. 1 is a color photograph showing a test plate having a test medium in accordance with the present invention. The test medium includes 6-chloroindolyl-β-D-galactoside and 5-bromo-4-chloro-3-indolyl-β-D-glucuronide. The test medium was inoculated with a mixture of E. coli and general coliforms and was incubated for 48 hrs. at 35° C. The photograph shows magenta-colored colonies, which are general coliforms and indigo blue-colored colonies, which are E. coli.

The method of the present invention allows the quantitative identification and differentiation of microorganisms having β-galactosidase but not β-glucuronidase activity and microorganisms having β-glucuronidase activity.

Microorganisms having β-galactosidase activity include those commonly known by the designation "coliform". There are various definitions of "coliform", but the generally accepted ones include bacteria which are members of the Enterobacteriaceae and have the ability to ferment lactose with gas production. The genera Citrobacter, Enterobacter, Klebsiella and Escherichia are the generally listed members of the coliform group.

Microorganisms having β-glucuronidase activity primarily include only those strains of coliform of the species Escherichia coli.

As used in this application, the term "general coliforms" refers to coliforms other than E. coli. These are microorganisms having β-galactosidase activity and not having β-glucuronidase activity.

The chromogenic β-galactosidase substrate is a β-galactoside comprising galactose joined by β-linkage to a substituent that forms an insoluble precipitate of a first color when liberated by the action of β-galactosidase on the substrate.

The chromogenic β-glucuronidase substrate is a β-glucuronide comprising glucuronic acid joined by β-linkage to a substituent that forms an insoluble precipitate of a second color, contrasting with the first color, when liberated by the action of β-glucuronidase on the substrate. The β-glucuronidase substrates and compounds described herein as "glucuronides" include carboxylate salts formed by reacting a suitable base with the glucuronic carboxyl group. Suitable bases include alkali metal or alkaline earth metal hydroxides or carbonates, for example, sodium hydroxide, potassium hydroxide, calcium hydroxide, magnesium hydroxide, and corresponding carbonates; and nitrogen bases such as ammonia and alkylamines such as trimethylamine, triethylamine and cyclohexylamine.

The β-galactosidase substrate and the β-glucuronidase substrate are selected so that the precipitates formed by each are of contrasting colors so that colonies of micro-organisms having β-galactosidase but not β-glucuronidase activity and colonies of microorganisms having β-glucuronidase activity can be visually distinguished. The exact color of each type of microorganism colony is not crucial as long as each type can be distinguished. The precipitates should be insoluble in the test medium so that the colonies of microorganisms producing each precipitate can be visually counted. Further, it will be readily appreciated that the β-galactosidase substrate and β-glucuronidase substrates should be compounds that are approximately colorless or are not deeply colored, so that they do not interfere with the detection of the colored insoluble precipitates produced by the action of β-galactosidase and β-glucuronidase. The substrates should be compounds that can be made soluble in the test medium. The determination of whether a given β-galactoside or β-glucuronide is operable can be made by a simple test comprising incubating the β-galactoside or β-glucuronide in an agar or pectin test medium inoculated with general coliforms or *E. coli* and observing whether colored colonies grow in the test medium. The determination of whether a given β-galactoside and β-glucuronide can be used together in the method of this invention and fall within the scope of the invention can be made by testing the two compounds together in a test medium inoculated with a mixture of both general coliforms and *E. coli* and observing whether the colonies of *E. coli* and the colonies of general coliforms can be visually differentiated by a contrast in color of each type of colony.

As an example of suitable compounds for the practice of the method of this invention, the compound 5-bromo-4-chloro-3-indolyl-β-D-galactopyranoside (X-gal) is a commercially available β-galactosidase substrate that produces an insoluble precipitate having an approximately indigo blue color when reacted upon by β-galactosidase. Possible β-glucuronidase substrates that could be used with 5-bromo-4-chloro-3-indolyl-β-D-galactopyranoside would be ones that produce an insoluble precipitate having a color such as red or yellow that contrasts with indigo blue and is not totally masked by the blue color. An example is the novel compound 6-chloroindolyl-β-D-glucuronide. This produces an insoluble precipitate having a magenta color contrasting with and visually distinguishable from indigo blue. The preparation of this compound is described below.

The compound 5-bromo-4-chloro-3-indolyl-β-D-glucuronide is a commercially available β-glucuronide substrate that produces an insoluble precipitate having an approximately indigo blue color when reacted upon by β-glucuronidase. Indoxyl-β-D-glucuronide is a similar compound, the preparation of which is described in Ley et al., Lan J. Microbiol. 39:690–693 (1987), the disclosure of which is hereby incorporated by reference. Possible β-galactosidase substrates that could be used with 5-bromo-4-chloro-3-indolyl-β-D-glucuronide or indoxyl-β-D-glucuronide would be ones that produce an insoluble precipitate having a color such as red or yellow that contrasts with indigo blue. An example is the novel compound 6-chloroindolyl-β-D-galactoside. This produces an insoluble precipitate having a magenta color contrasting with and visually distinguishable from indigo blue. The preparation of this compound is described below.

Preparation of Novel β-galactosidase and β-glucuronidase Substrates

The Following Illustrates the Synthesis of 6-chloroindolyl-β-D-galactoside:

1. 4-Chloroanthranilic acid:

4-Chloroanthranilic acid was prepared from 5-chloro-2-methylaniline as described by James R. Piper and Frank J. Stevens in "Substituted Indole-3-acetic acids by the Reformatsky Reaction" and published in the Journal of Organic Chemistry, Volume 27, pp. 3134–3137.

A solution of 70.8 g (0.5 M) 5-chloro-2-methylaniline in 70 ml glacial acetic acid was treated with 52 g (0.51 M) acetic anhydride and brought to gentle reflux for 30 minutes. The solution was poured into 400 ml cold water and the n-acetyl-5-chloro-2-methylaniline that separated was filtered off and washed with cold water.

The damp acetyl derivative was suspended in 2 L 0.25 M magnesium sulfate solution at 85° C. With vigorous stirring, 240 g potassium permanganate as added, portionwise, over a 1.5 hour period, keeping the temperature between 85 and 90° C. The mixture was filtered hot, and the manganese dioxide by-product was washed with 1 L hot water. The aqueous filtrate was cooled to room temperature and acidified with 20% sulfuric acid to a pH of 1, precipitating n-acetyl-4-chloroanthranilic acid. The product was filtered off and washed with cold water.

The damp n-acetyl-4-chloroanthranilic acid was suspended in 400 ml of concentrated hydrochloric acid (12 M) and stirred and heated at 80° C. for 8 hours. The mixture was cooled to 10° C. and the resulting 4-chloroanthranilic acid hydrochloride was filtered off. The solid was suspended in 300 ml water and sodium acetate was added, portionwise until the pH was 5. The resulting 4-chloroanthranilic acid was filtered off and recrystallized from the minimum of hot ethanol. The final yield of off-white crystals was 50 g, melting at 239–240° C.

2. 5-Chloro-2-carboxyphenylglycine sodium salt:

4-Chloroanthranilic acid weighing 474 g (2.69 M) was suspended in 1200 ml water in a 5 L flask. A 30% potassium hydroxide solution was added, slowly, with stirring, until the pH was 7.0 to 8.0. The 4-chloro-anthranilic acid dissolved to form a solution of the potassium salt. To this solution, was added a solution of 326.5 g (2.80 M) of sodium monochloroacetate in 800 ml water. The resultant solution was then placed in a pressure bottle and allowed to stand at 60° C. for three days. The product precipitated and the mixture was almost solid after three days. The product was filtered off and washed with 200 ml ice cold water. After drying in vacuo, the off white product weighed 335 g (43% yield) and melted at 278–280° C.

3. 6-Chloroindoxyl-1,3-diacetate:

Into a 5 L, 3-neck flask equipped with mechanical stirring, reflux condenser and gas evolution bubbler was placed 335 g (1.33 M) of 5-chloro-2-carboxyphenylglycine sodium salt, 2.3 1 acetic anhydride and 421 g of anhydrous sodium acetate. The mixture was brought to reflux and maintained for 3 hours until the evolution of carbon dioxide was nearly complete. The mixture was placed in a beaker while hot and chilled to 0° C. overnight. The next day, the product was filtered off and mixed with 2 L water and stirred for 1 hour to hydrolyze any residual acetic anhydride. The solid was filtered off and washed with water and then dried in vacuo. This crude material, when dry, was dissolved in the minimum of hot ethyl acetate and allowed to crystallize overnight at 0° C. After filtering and washing with a little cold hexane, and drying in vacuo, the product weighed 150 g and had a melting point of 112–113° C.

4. 6-Chloro-N-acetylindol-3-ol:

A solution of 572 ml of concentrated sulfuric acid was added to 63 ml of water with stirring and cooling. When the acid solution was at room temperature, 134 g (0.53 M) of 6-chloroindoxyl-1,3-diacetate was added, portionwise, with stirring over a period of one hour keeping the temperature of the solution between 20 to 25° C. After stirring for 30 additional minutes after the addition was complete, the solution was poured onto 2 kg ice. The ice was allowed to melt and the insoluble product was filtered off and washed with cold water. This product was then protected from light and air and dried in a vacuum oven at room temperature. The yield of light yellow solid was 110 gm. This product was very unstable and could not be stored for long period without decomposition. It was used immediately in the next step.

5. 6-Chloroindolyl-β-D-galactoside pentaacetate:

Into a 1 L, 3-neck flask, equipped with a mechanical stirrer and a gas sparger tube was added 250 ml dry methanol, followed by 2.3 g (0.1 M) of sodium metal. While the sodium was reacting, a nitrogen sparge was started at the rate of 1 bubble per second. When the sodium had dissolved, the solution was cooled to 0° C. and 20.9 g (0.1 M) of 6-chloro-N-acetylindol-3-ol was added, maintaining nitrogen purge throughout. After stirring for 10 minutes, 41.1 g (0.1 M) of acetobromogalactose was added all at once. The reaction was allowed to proceed for 5 hours, slowly warming up to room temperature. The by-product of sodium bromide was filtered off and the solution was evaporated in vacuo to leave a gum. This gum was dissolved in ethyl acetate and then extracted with water in a separatory funnel. The organic phase was dried over sodium sulfate, filtered and evaporated in vacuo once again. The residue was dissolved in the minimum of hot ethanol and allowed to cool slowly to room temperature. The product crystallized as fine white needles and was filtered off and dried. The yield was 18 g melting at 165–166° C.

6. 6-Chloroindolyl-β-D-galactoside:

6-Chloroindolyl-β-D-galactoside pentaacetate 10 g (0.018 M) was suspended in 250 ml of dry methanol. To the suspension was added a solution of 100 mg sodium metal dissolved in 10 ml dry methanol. The mixture immediately formed a clear solution. After standing for 1 hour at room temperature, the solution was evaporated in vacuo to a low volume and stored at 0° C. overnight. The next day, the crystalline product was filtered off and washed with ethyl ether and dried in vacuo. The yield was 2.5 g white crystals that melted at 100–102° C.

The following illustrates the synthesis of 6-chloroindolyl-β-D-glucuronic acid monocyclohexylammonium salt.

Steps 1–4 are identical to the above steps 1–4 in the synthesis of 6-chloroindolyl-β-D-galactoside.

5. Methyl[6-chloro-N-acetylindol-3-yl-(2,3,4-tri-O-acetyl-β-D-glucopyranoside)] uronate:

To 100 ml of dry methanol at −5° C. containing 1.8 g of sodium metal was added 16.34 g (0.078 M) of 6-chloro-N-acetylindol-3-ol under an atmosphere of nitrogen. The solution was cooled and maintained at 0° C. while adding a solution of 31 g (0.08 M) of 1-bromo-1-deoxy-2,3,4-tri-O-acetyl-α-D-glucopyranuronate in 150 ml of dry methanol all at once. The mixture was allowed to warm to room temperature while stirring under nitrogen for four hours. The mixture was then sparged with air and unreacted indoxyl was converted to insoluble indigo. The mixture was filtered and the filtrate was evaporated to a gum in vacuo. The gummy residue was dissolved in ethyl acetate (approx. 200 ml) and washed in a separatory funnel with 200 ml water. The organic phase was separated, filtered and evaporated to a gum. The residue was taken up in 28 ml of acetic anhydride and 40 ml of pyridine and allowed to stand at room temperature overnight. The solution was poured into 600 ml water and allowed to stand until the product had solidified. The product was filtered off and crystallized from the minimum of boiling ethanol. White crystals, melting at 172° C. were obtained. The yield was 11 grams.

6. 6-Chloroindolyl-β-D-glucopyranoside uronate monocyclohexylammonium salt:

To 400 ml of acetone containing 10 g of methyl-(6-chloroindol-3-yl-2,3,4-tri-O-acetyl-β-D-glucopyranoside) uronate was added 100 ml of 1 N sodium hydroxide. The solution was stirred at room temperature for 20 minutes and then evaporated in vacuo to approximately 150 ml volume. The solution was adjusted to pH 7.5 with dilute acetic acid and then treated with stirring with a saturated solution of lead acetate. The lead salt of the product was collected by filtration and immediately suspended in 100 ml of methanol. To this stirred suspension of lead salt was added hydrogen sulfide gas until the lead was converted into lead sulfide. The lead salt was removed by filtration and the filtrate containing the product was evaporated to approximately 50 ml in vacuo. A solution of 1 ml of cyclohexylamine in 10 ml methanol was added and upon cooling the amine salt started to crystallize. The methanol suspension of product was diluted with one volume of ethyl ether and filtered. The product consisted of 2 g of off-white crystals melting at 211–213° C.

Other novel β-galactosidase and β-glucuronidase substrates:

Other β-galactosides and β-glucuronides that may be useful in the method of this invention include those that fall into the general category of substituted indolyl β-galactosides and β-glucuronides. While it is not intended to limit this invention to any particular theory or mechanism, it is believed that when β-galactosidase or β-glucuronidase substrates having substituted indolyl substituents are reacted upon by their respective enzymes, the substituted indolyl substituents released by the action of the enzyme convert in situ to insoluble indigo analogues. For example, when 6-chloroindolyl-β-D-galactoside is reacted upon by β-galactosidase, the released 6-chloroindolyl reacts with itself and forms 6,6'-dichloroindigo, a magenta insoluble precipitate. This suggests that other compounds similar to 6-chloroindolyl-β-D-galactoside or 6-chloroindolyl-β-D-glucuronide could be made based upon symmetrical indigo analogues having a color similar to 6,61'-dichloroindigo. The synthesis and absorption spectra of symmetrical chloroindigos were reported in Sadler et al., JACS 78-1251–1255 (1956), the disclosure of which is incorporated herein by reference. It appears therein that the compounds 4,4',6,6' tetrachloroindigo, 6,6', 7,7' tetrachloroindigo, and 4,4',6,6', 7,7' hexachloroindigo are similar in color to 6,6'-dichloroindigo. Thus, the respective β-galactosides namely 4,6-dichloroindolyl-β-D-galactoside, 6,7-dichloroindolyl-β-D-galactoside, and 4,6,7-trichloroindolyl-β-D-galactoside could be made and used as β-galactosidase substrates in the same manner as 6-chloroindolyl β-D-galactoside. Similarly, the respective β-glucuronides, namely 4,6-dichloroindolyl-β-D-glucuronide, 6,7-dichloroindolyl-β-D-glucuronide, 4,6, 7-trichloroindolyl-β-D-glucuronide, could be made and used as β-glucuronidase substrates in the same manner as 6-chloroindolyl-β-D-glucuronide.

Preparation of Test Medium

The test medium is formed by combining the β-galactosidase substrate and the β-glucuronidase substrate with a nutrient base medium. The nutrient base medium can be any culture medium known in the art for growing microorganisms. Generally such media include growth nutrients, buffers, water, and a gelling agent. Possible gelling agents include agars, pectins, carrageenans, alginates, locust bean, and xanthins, among others.

The following is an example of the preparation of a test medium suitable for use in this invention.

To prepare sufficient quantity of the β-galactosidase substrate and the β-glucuronidase substrate for one liter of medium, 150 mg of the β-galactosidase substrate and 75 mg of the β-glucuronidase substrate are weighed and added to 5 ml of dimethylformamide (DMF). The mixture is agitated until dissolved. An additional 10 ml of deionized water is added mixed. The mixture is filter sterilized with a micropore filter.

Standard agar medium may be made by adding 15 gm of bacteriological quality agar gum to the following nutrient formula Pancreatic Digest of Casein—5.0 gm Yeast Extract—3.0 gm Dipotassium Phosphate—0.3 gm Deionized Water—1000 ml and then sterilizing at 121° C. for 15 minutes. The medium should be adjusted to result in a pH of 7.0. The sterilized agar medium is allowed to drop to a temperature of 45° C. in a water bath and then the sterile solution containing 150 mg of the β-galactosidase substrate and 75 mg of the β-glucuronidase substrate is added. The medium is mixed thoroughly and poured into sterile petri plates at a volume of 20 ml/plate.

A pectin-based test medium may be prepared using the same steps described above except that 25 gm of low methoxyl pectin is used as the solidifying agent and the medium is poured at room temperature into petri plates containing a thin gel layer containing calcium ions which combine with the pectin to form a solid gel. A suitable pectin culture medium is described in U.S. Pat. No. 4,241,186 and U.S. Pat. No. 4,282,317, the disclosures of which are incorporated herein by reference. A pectin-based medium is preferred over a standard agar medium because it has the advantages of convenience and temperature independence for the user. The use of pectin media is well described and accepted as a result of AOAC collaborative studies and other published and in-house investigations.

A suitable pectin medium is commercially available from RCR Scientific, Inc. under the trademark Redigel.

Inoculation of the Test Medium with the Sample

The test medium may be inoculated with a sample to be tested for the presence of microorganisms having β-galactosidase but not glucuronidase activity and microorganisms having β-glucuronidase activity by any method known in the art for inoculating a medium with a sample containing microorganisms. For example, the sample to be tested may be added to the petri plates prior to adding the nutrient base medium (pour plate technique) or spread on the surface of the plates after they have cooled and solidified (swab or streak plate technique).

Incubation of the Test Medium

The inoculated test medium is incubated for a sufficient time and at such a temperature for individual microorganisms present in the sample to grow into detectable colonies. Suitable incubation conditions for growing microorganisms in a medium are known in the art. Preferably, the test medium is incubated for about 24–48 hours at a temperature of about 30–40° C.

Unless inhibitors of the general microbial population are used, the general microbial population as well as general coliforms and *E. coli* will grow in the incubated test medium. Because microorganisms other than general coliforms and *E. coli* rarely produce β-galactosidase or β-glucuronidase, the general microbial population will show as it does on a standard agar pour plate as white or colorless colonies. General coliforms produce β-galactosidase, which acts upon the β-galactosidase substrate in the test medium, causing the β-galactosidase substrate to form an insoluble precipitate having a color in accordance with the particular β-galactosidase substrate used. Because the precipitate formed is insoluble in the test medium, it remains in the immediate vicinity of microorganisms producing the β-galactosidase. As the microorganisms reproduce to form colonies, the colonies show as colonies having the color produced by the β-galactosidase substrate.

*E. coli* produces β-galactosidase, but, unlike general (other) coliforms, also produces β-glucuronidase. Insoluble precipitates of both the β-galactosidase substrate and β-glucuronide substrate are formed by the action of the respective enzymes. The colonies of *E. coli* show as colonies having a color different from and contrasting with the color of the colonies of general coliforms because of the presence of the contrastingly colored insoluble precipitate of the β-glucuronidase substrate. Preferably, the β-galactosidase substrate and the β-glucuronidase substrate are selected so that the β-glucuronidase substrate produces an insoluble precipitate that is darker in color than the insoluble precipitate produced by the β-galactosidase substrate. This would allow the precipitate produced by the β-glucuronidase substrate to mask the precipitate produced by the β-galactosidase substrate in colonies of *E. coli* and would make it easier for colonies of *E. coli* to be differentiated from colonies of general coliforms. Preferably 6-chloroindolyl-β-D-galactoside is used with 5-bromo-4-chloro-3-indolyl-β-D-glucuronide or indoxyl-β-D-glucuronide.

Examination of the Test Medium and Enumeration of Microorganisms

Since the β-galactosidase substrate and the β-glucuronidase substrate are selected so that the colors of the precipitate produced by each contrast with each other, the colonies of each type of coliform, general coliforms and *E. coli*, can be readily differentiated by visual means. For example, if 6-chloroindolyl-β-D-galactoside is used as the β-galactosidase substrate and 5-bromo-4-chloro-3-indolyl-β-D-glucuronide is used as the β-glucuronide substrate, general coliforms will show as magenta-colored colonies and *E. coli* as indigo blue-colored colonies.

The colonies of each type of microrganism may be enumerated by counting the colonies or by other methods known in the art for enumerating microorganisms on a test plate. The number of colonies of each type indicates the number of microorganisms of each type originally present in the sample before incubation.

Optional Ingredients

Inhibitors

The method of the present invention does not require inhibitors. However, the medium may be made more selective for general coliforms and *E. coli* if desired by the addition of various compounds that are inhibitory to the general microbial population, but have little or no effect on coliforms. Following are some compounds which may be used: a) bile salts, about 0.3 g/liter, b) sodium lauryl sulfate, about 0.2 g/liter, c) sodium desoxycholate, about 0.2 g/liter, d) Tergitol 7, about 0.1 ml/liter. The use of one or more of these compounds reduces the background (non-coliform) microorganism presence and makes a less cluttered plate and eliminates the possibility of inhibition or interference by the non-coliform organisms in the sample.

Inducers

It is possible that the enzyme production of the general coliforms may be enhanced by the addition to the medium formulations of very small amounts of substances known as enzyme inducers. The specific inducer for β-galactosidase is available and is known chemically as isopropyl-β-D-thiogalactopyranoside. Adding approximately 25 mg/liter of medium has a positive and noticeable effect on the speed of enzyme production for some species of coliforms.

EXAMPLE 1

6-Chloroindolyl-β-D-galactoside and 5-bromo-4-chloro-3-indolyl-β-D-glucuronide (X-gluc) were each tested separately with 17 different bacterial species including β-galactosidase producing microorganisms, β-glucuronidase producing microorganisms, and microorganisms which produce neither enzyme.

As shown in Table I below, only *E. coli* grew as indigo blue colonies in the X-gluc medium (as indicated by a + in the X-gluc column). *E. coli, Enterobacter aerogenes, Enterobacter cloacae, Citrobacter freundii* and *Klebsiella pneumoniae* grew as magenta colonies in the medium containing 6-chloroindolyl-β-D-galactoside (as indicated by a + in this column). All the other species grew as colorless colonies on both media, as would be expected (as indicated by a – in the respective columns).

TABLE I

| Species | 6-chloroindolyl-β-D-galactoside | X-gluc |
| --- | --- | --- |
| Acinetobacter calcoaceticus | – | – |
| Bacillus cereus | – | – |
| Bacillus megaterium | – | – |
| Bacillus subtilis | – | – |
| Citrobacter freundii | + | – |
| Enterobacter aerogenes | + | – |
| Enterobacter cloacae | + | – |
| Escherichia coli | + | + |
| Klebsiella pneumoniae | + | – |
| Proteus vulgaris | – | – |
| Pseudomonas aeruginosa | – | – |
| Salmonella typhimurium | – | – |
| Sarcina lutea | – | – |
| Serratia marcescens | – | – |
| Staphylococcus aureus | – | – |
| Staphylococcus epidermidis | – | – |
| Staphylococcus faecalis | – | – |

EXAMPLE 2

Test plates containing both 6-chloroindolyl-β-D-galactosidase and 5-bromo-4-chloro-3-indolyl-β-D-glucuronidase in a pectin gel medium were prepared. The test plates were inoculated with natural river water or with mixes of *E. coli* and other coliforms (*E. aerogenes* and *K. pneumoniae*).

Agar and pectin (Redigel) test plates were also prepared for the Violet Red Bile (VRB) test for coliforms using standard procedures. These plates were also inoculated with river water or mixes of *E. coli* and other coliforms.

The test plates were incubated and then examined. The results are shown in Table II below. The numbers in each column represent the number of colonies of each type per test plate. The number of colonies of each type per test plate ultimately corresponds to the number of individual microorganisms of each type present in the sample before incubation.

| | Mixture of 6-chloroindolyl-β-D-galactoside and 5-bromo-4-chloro-3-indolyl-β-D-glucuronide | | | | |
| --- | --- | --- | --- | --- | --- |
| | Red | Blue | Total | VRB Agar Total Count | VRB Redigel Total Count |
| | | | RUN 1 | | |
| River 1 | 260 | — | 260 | 290 | 325 |
| River 2 | 305 | 5 | 310 | 290 | 350 |
| Mix 1 | 28 | 10 | 38 | 5 | 41 |
| Mix 2 | 31 | 6 | 37 | 7 | 24 |

Mix 1 and 2 are *E. coli* (blue) and *Enterobacter aerogenes* (red)

| | | | RUN 2 | | |
| --- | --- | --- | --- | --- | --- |
| River 1 | 4 | 31 | 36 | | 38 |
| River 2 | 4 | 42 | 46 | | 26 |
| Mix 1 | 10 | 70 | 80 | | 90 |
| Mix 2 | 7 | 90 | 97 | | 90 |

Mix 1 and 2 are *E. coli* (blue) and *Klebsiella pneumoniae* (red)

As shown above, the total counts of coliforms indicated by the test medium of the present invention are in approximate agreement with the results obtained with the VRB tests. However, the present method has the advantage of differentiating *E. coli* from general coliforms, so that a separate total of each may be obtained. With VRB, further tests would be required to determine if any of the colonies were *E. coli*, requiring further time and expense.

EXAMPLE 3

A test plate containing 6-chloroindolyl-β-D-galactosidase and 5-bromo-4-chloro-3-indolyl-β-D-glucuronide in a pectin gel medium was inoculated with a sample containing *E. coli* and general coliforms. The plate was incubated for 48 hours at 35° C. and then examined for the presence of magenta-colored colonies and indigo blue-colored colonies. FIG. 1 is a photograph of the test plate as it appeared after 48 hours. As shown in FIG. 1, the indigo blue colonies of *E. coli* are easily distinguished by visual means from magenta colonies of general coliforms. The number of colonies of each type of microorganisms is easily counted—there are 13 colonies of *E. coli* and 52 colonies of general coliforms.

Although the invention has been described in considerable detail with specific reference to certain advantageous embodiments thereof, variations and modifications can be made without departing from the scope of the invention as described in the specification and defined in the appended claims.

What is claimed is:

1. A test medium for detecting the presence of biological material having β-galactosidase enzyme specificity, said test medium comprising:
   a base medium for maintenance of said biological material; and
   a chromogenic indolyl β-galactoside substrate forming an insoluble compound of a first color upon reacting with β-galactosidase, wherein said chromogenic β-galactoside substrate is selected from the group consisting of 6-chloroindolyl-β-D-galactoside, 4,6-dichloroindolyl-β-D-galactoside, 6,7-dichloroindolyl-β-D-galactoside, 4,6,7-trichloroindolyl-β-D-galactoside and salts thereof.

2. The test medium of claim 1, further comprising chromogenic β-glucuronide substrate forming an insoluble compound of a second color upon reacting with β-glucuronidase.

3. The test medium of claim 1, wherein said base medium is a solid, gel or liquid for forming a solid.

4. The test medium of claim 1, further comprising 5-bromo-4-chloro-3-indolyl-β-D-glucuronide.

5. The test medium of claim 1, further comprising a chloro-substituted indolyl β-glucuronide.

6. The test medium of claim 5, wherein said β-glucuronide is selected from the group consisting of 6-chloroindolyl-β-D-glucuronide, 4,6-dichloroindolyl-β-D-glucuronide, 6,7-dichloroindolyl-β-D-glucuronide, 4,6,7-trichloroindolyl-β-D-glucuronide and salts thereof.

7. A test medium for detecting the presence of biological material having β-glucuronidase enzyme specificity, said test medium comprising:
    a base medium for maintenance of a biological material having enzyme specificity, and
    a chromogenic indolyl β-glucuronide substrate forming an insoluble compound of a first color upon reacting with β-glucuronidase.

8. The test medium of claim 7, wherein said β-glucuronide substrate is selected from the group consisting of 6-chloroindolyl-β-D-glucuronide, 4,6-dichloroindolyl-β-D-glucuronide, 6,7-dichloroindolyl-β-D-glucuronide, 4,6,7-trichloroindolyl-β-D-glucuronide and salts thereof.

9. The test medium of claim 7, further comprising a chromogenic 5-bromo-4-chloro-3-indolyl-β-D-galactopyranoside substrate for forming a water insoluble compound of a second color upon reacting with β-galactosidase.

10. A method for testing the presence of and quantitatively identifying and differentiating microorganisms in a biological test sample, said test sample containing first microorganisms having β-galactosidase but not β-glucuronidase activity, and second microorganisms having β-glucuronidase activity comprising the steps of
    inoculating a solid test medium or substrate capable of forming a solid with said test sample, said test medium comprising a chromogenic β-galactoside substrate capable of forming a first water-insoluble precipitate of a first color upon reacting with β-galactosidase, a chromogenic β-glucuronide substrate capable of forming a second water-insoluble precipitate of a second color contrasting with said first color upon reacting with β-glucuronidase, and a base medium, said first and second colors being visibly distinguishable in daylight,
    incubating said test medium to produce colonies of said first and second microorganisms and first and second colored precipitates corresponding to said colonies,
    examining said test medium for the presence of colonies having said first color, such colonies being colonies of microorganisms having β-galactosidase but not β-glucuronidase activity, and the presence of colonies having said second color, such colonies being colonies of microorganisms having β-glucuronidase activity, and
    enumerating said colonies of microorganisms having β-galactosidase activity and said colonies of microorganisms having β-glucuronidase activity.

11. The method of claim 10, wherein said chromogenic β-galactoside substrate is selected from the group consisting of 6-chloroindolyl-β-D-galactoside, 4,6-dichloroindolyl-β-D-galactoside, 6,7-dichloroindolyl-β-D-galactoside, 4,6,7-trichloroindolyl-β-D-galactoside and salts thereof.

12. The method of claim 11, wherein said β-glucuronide is 5-bromo-4-chloro-3-indolyl-β-D-glucuronide or indoxyl-β-D-glucuronide.

13. The method of claim 10, wherein said chromogenic β-glucuronide is at least one selected from the group consisting of 6-chloroindolyl-β-D-glucuronide, 4,6-dichloroindolyl-β-D-glucuronide, 6,7-dichloroindolyl-β-D-glucuronide, 4,6,7-trichloroindolyl-β-D-glucuronide and salts thereof.

14. The method of claim 13, wherein said β-galactoside substrate is 5-bromo-4-chloro-3-indolyl-β-D-galactoside.

15. A method for testing the presence of and quantitatively identifying and differentiating microorganisms in a biological test sample containing first and second microorganisms having enzyme activity, comprising the steps of
    inoculating a solid test medium or substrate capable of forming a solid with said test sample, said test medium comprising a first chromogenic substrate capable of forming a first water insoluble precipitate of a first color upon reacting with said first microorganism, a second chromogenic substrate capable of forming a second water insoluble precipitate of a second color contrasting with said first color upon reacting with said second microorganism, and a base medium, said first and second colors being visibly distinguishable in daylight,
    incubating said test medium to produce colonies of said first and second microorganisms and first and second colored precipitates corresponding to said colonies,
    examining said test medium for the presence of colonies of said first microorganisms having said first color, and the presence of colonies of said second microorganisms having said second color, and
    enumerating said colonies of said first and second microorganisms.

16. The test medium of claim 15, wherein said first chromogenic substrate is a β-galactoside substrate selected from the group consisting of 6-chloroindolyl-β-D-galactoside, 4,6-dichloroindolyl-β-D-galactoside, 6,7-dichloroindolyl-β-D-galactoside, 4,6,7-trichloroindolyl-β-D-galactoside and salts thereof.

17. The method of claim 16, wherein said second chromogenic substrate is a β-glucuronide substrate.

18. A test medium for detecting the presence of biological material containing first and second microorganisms having enzyme specificity, said test medium comprising:
    a base medium for maintenance of said biological material;
    a first chromogenic substrate forming an insoluble compound of a first color upon reacting with said first microorganism; and
    a second chromogenic substrate forming an insoluble compound of a second color upon reaction with said second microorganism.

19. The test medium of claim 18, wherein said first chromogenic substrate is a β-galactoside substrate selected from the group consisting of 6-chloroindolyl-β-D-galactoside, 4,6-dichloroindolyl-β-D-galactoside, 6,7-dichloroindolyl-β-D-galactoside, 4,6,7-trichloroindolyl-β-D-galactoside and salts thereof.

20. The test medium of claim 19, wherein said second chromogenic substrate is a β-glucuronide.

* * * * *